(12) United States Patent
Oosterhoff

(10) Patent No.: US 7,135,591 B2
(45) Date of Patent: Nov. 14, 2006

(54) ADHESIVE BASED ON BIODEGRADABLE ACRYLATES

(75) Inventor: Rudolph Hendrik Oosterhoff, Ede (NL)

(73) Assignee: Lijmtechniek B.V., Ede (NL)

( * ) Notice: Subject to any disclaimer, the term of this patent is extended or adjusted under 35 U.S.C. 154(b) by 84 days.

(21) Appl. No.: 10/928,637

(22) Filed: Aug. 27, 2004

(65) Prior Publication Data

US 2005/0085608 A1   Apr. 21, 2005

(30) Foreign Application Priority Data

Aug. 29, 2003   (NL) ................................. 1024200

(51) Int. Cl.
*C07C 69/74* (2006.01)
*C08J 3/00* (2006.01)
*C08L 31/02* (2006.01)
*C08F 118/02* (2006.01)

(52) U.S. Cl. .................. 560/128; 560/205; 524/439; 524/556; 526/319

(58) Field of Classification Search ................ 526/319; 560/190, 128, 205; 524/439, 556
See application file for complete search history.

(56) References Cited

U.S. PATENT DOCUMENTS

| | | | | |
|---|---|---|---|---|
| 3,152,894 A | * | 10/1964 | Tinker et al. ................. | 430/87 |
| 3,394,029 A | * | 7/1968 | MacArthur ................. | 428/518 |
| 4,424,240 A | * | 1/1984 | Kielbania, Jr. ........... | 427/393.5 |
| 4,709,084 A | * | 11/1987 | Pavlin et al. ............... | 560/118 |
| 5,759,569 A | * | 6/1998 | Hird et al. .................. | 424/443 |
| 2004/0171727 A1 | * | 9/2004 | Winters et al. ............. | 524/270 |

FOREIGN PATENT DOCUMENTS

| | | |
|---|---|---|
| EP | 0 745 653 A1 | 12/1996 |
| JP | 8 218039 A | 8/1996 |
| NL | 9 201 695 A | 4/1994 |

* cited by examiner

*Primary Examiner*—David W. Wu
*Assistant Examiner*—M. Bernshteyn
(74) *Attorney, Agent, or Firm*—The Webb Law Firm

(57) ABSTRACT

The invention relates to an acrylate monomer of Formula 1

$$Dtp-COO-(CH_2)_n-O-CO-CH=CH_2$$

wherein
Dtp is a diterpene group derived from a resin acid and
n is a number from 2–4
as well as a process for the preparation thereof.
The resin acid is in particular abietic acid or an isomer thereof.
These monomers and the prepolymers and polymers derived therefrom can be used as biodegradable adhesives for materials such as metal, plastic, glass, paper and wood, in particular as construction adhesive.

11 Claims, No Drawings

ADHESIVE BASED ON BIODEGRADABLE ACRYLATES

The invention relates to an adhesive that contains a monomer containing acrylate groups bound to a naturally occurring, biodegradable group, or a polymer thereof The invention relates in particular to construction adhesives allowing components that are often of high quality and are made of metal, plastic, glass and wood to be glued.

BACKGROUND

A requirement that is becoming increasingly important in respect of adhesives is that they not only have good bonding properties but are also biodegradable. However, the known adhesives do not meet this requirement to a sufficient extent: powerful adhesives are generally not biodegradable or are biodegradable to only a slight extent.

An adhesive layer that contains a copolymer of an abietinoyl-glyceryl(meth)acrylate, an alkyl acrylate and a polyethylene glycol(meth)acrylate is described in European Patent EP 0 745 653. The adhesives concerned here are contact adhesives and not construction adhesives. There is also no mention of any biodegradability of the adhesive layers.

Netherlands Patent Application 9201695 (patent number 195014) corresponding to U.S. Pat. No. 5,580,940 discloses a biodegradable diacrylate with a sugar as central unit. These known diacrylates comply, for example, with the formula:

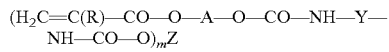

wherein A is a $C_2$–$C_4$ alkylene group, R is hydrogen or methyl, Y is an alicyclic group, in particular an isophoronediyl group and Z is a sugar residue, such as a glucose or fructose residue. As a result of the sugar residue, too high a solubility in water is produced, as a result of which the polymer is less suitable for construction adhesives for metal, plastic, glass and wood, The size of the side groups (isophoronediyl and sugar) on the reactive acrylate also means that the polymer will be weak and soft, which is very suitable for paper and cardboard and for contact adhesives, but not for construction adhesives.

In the known products, insofar as they are biodegradable adhesives, the adhesive characteristics are inadequate for construction adhesives and the application possibilities are restricted.

SUMMARY OF THE INVENTION

A group of monomers has now been found that are suitable as a basis for biodegradable adhesives with good bonding properties. The monomers are acrylate monomers in which the acrylate group is bound to a resin acid via an alkylene bridge. The monomers comply with the formula:

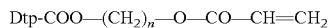

wherein
Dtp is a diterpene group derived from a resin acid and
n is a number from 2–4.

DETAILED DESCRIPTION OF THE INVENTION

The diterpene group Dtp is derived from a resin acid having approximately 20 carbon atoms from rosin (colophony). These resin acids include mono- or poly-unsaturated, tricyclic monocarboxylic acids such as abietic acid ($C_{20}H_{30}O_2$) and stereo-and regio-isomers and dehydro and dihydro derivatives thereof, such as neoabietic acid, dehydroabietic acid, dihydroabietic acid, pimaric acid, laevopimaric acid, isopimaric acid and palustric acid. In general the decarboxylated radicals Dtp derived from these acids have the empirical formula $C_{19}H_{27}$, $C_{19}H_{29}$ or $C_{19}H_{31}$.

The diterpene group is coupled to the acrylate unit via an alkylene bridge having the formula $(CH_2)_n$. This alkylene bridge can be an ethylene, 1,2-propylene, 1,2-butylene, trimethylene or tetramethylene group. Preferably, the alkylene bridge is an ethylene group, which, for example, is accessible in the form of a hydroxyethyl acrylate.

The acrylate unit is preferably an unsubstituted acrylate group, i.e. preferably not a methacrylate group, because it has been found that the bonding speed of the product containing an acrylate group according to the invention is better than in the corresponding products containing a methacrylate group or an acrylate group substituted in some other way.

The monomers according to the invention can be obtained by reaction of a suitable hydroxyalkyl acrylate with a resin acid or reactive derivative thereof, such as an ester, an anhydride or a halide, under conventional esterifying or transesterifying conditions, for example in the presence of an acid. Further features of the synthesis are to be found in the examples.

The invention also relates to adhesives based on polymers that have been obtained by polymerisation of an acrylate monomer as described above. Such a polymer can be a homopolymer of the formula:

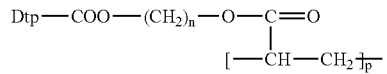

It can also advantageously be an acrylate copolymer of the formula

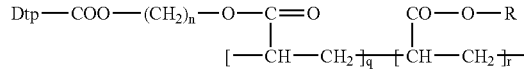

In this formula Dtp and n have the definitions given above, R is hydrogen or a $C_1$–$C_4$ alkyl group optionally substituted by hydroxyl, alkoxy or acyloxy, p is a number from 2 or more and q and r independently of one another are a number from 1 or more.

Copolymers with other monomers, for example in which the group CO—O—R has been replaced by another group such as hydrogen(ethylene), methyl(propylene), vinyl(butadiene), phenyl(styrene) or acetoxy(vinyl acetate) also provide usable products.

Here the term polymers must be understood to mean all macromolecular compounds in which at least two acrylate units according to the invention are present. Prepolymers and oligomers are thus also included.

The polymers according to the invention can be obtained by polymerisation of the acrylates described above in a manner known per se, for example by polymerisation with thermal initiators such as peroxides and hydroperoxides, for example benzoyl peroxide, lauroyl peroxide, butyl hydroperoxide, azo compounds such as azoisobutyro-nitrile and the like. The polymers can also be obtained by polymerisation with photo-chemical initiators, such as benzophenone, benzoin, (di)sulphides and thiols.

The monomer or prepolymer according to tie invention is exceptionally suitable for use as monomer adhesive. For this purpose the prepolymer is mixed in combination with an organic peroxide or with a photochemical initiator and used directly as adhesive for metal, plastic, ceramic, glass and other materials. Such a monomer adhesive is particularly suitable as construction adhesive.

However, the monomer or prepolymer according to the invention can also be polymerised via, for example, emulsion polymerisation in water. A polymer dispersion of the polymer in water is then produced. This product can be used as such as quick-drying packaging adhesive, wood adhesive, plastic adhesive and the like. Such a quick-drying packaging adhesive can be used on high-speed packing machines.

In addition to the monomer or polymer, the adhesives according to the invention can also contain other auxiliaries, such as diluents, thickeners, stabilisers, heat-conducting, insulating or fire-retardant agents or—in particular in the case of electronic applications—electrically conducting materials such as conducting polymers and metals, Such auxiliaries can be present on their own or in combination in an amount of, for example, 2–2000% with respect to the acrylate monomer or polymer. By way of example, an electrically conducting adhesive according to the invention can contain 1–10 parts by weight of a metal such as copper, silver, gold or another transition metal per part by weight terpenyl acrylate.

EXAMPLES

Example 1

Preparation of Abietoyloxyethyl Acrylate

Abietic acid (302 g, 1 mol) was activated with 1 mol oxalyl chloride in a solution in toluene, Hydroxyethyl acrylate (128 g, 1.1 mol) and 1000 ppm MEHQ (4-methoxy-phenol, 0.1 g) were added thereto and the mixture was stirred for 3–4 hours at 40° C. Hydrochloric acid was removed by polymer-bound sodium carbonate and filtered off. The product was isolated by distilling off the toluene solvent. $^1$H-NMR spectroscopy confirmed the structure of the title compound.

Example 2

Peroxide-curing Adhesive for Electronic Applications

The following constituents were mixed:

| | |
|---|---|
| Abietoyloxyethyl acrylate (Example 1) | 100 g |
| Hydroxypropyl acrylate | 50 g |
| Silane acrylate | 1–5 g |
| Butyl peroxide adduct | 1–5 g |
| Silver powder | 450 g |

The adhesive is filled into glue cartridges and metered out using air pressure or applied by screen printing.

Example 3

| UV-curing adhesive for glass | |
|---|---|
| Abietoyloxyethyl acrylate (Example 1) | 100 g |
| TPGDA (tripropylene glycol diacrylate) | 50 g |
| Acrylic acid | 5 g |
| Silane acrylate | 3 g |
| Irgacure 184 | 5 g |

Example 4

Emulsion Polymerisation of Abietoyloxyethyl Acrylate

The following phases were introduced into a 250 ml three-necked flask provided with a dropping funnel, thermometer and stinter.

| Phase 1 | |
|---|---|
| 10% polyvinyl alcohol in water | 15 g |
| demineralised water | 10 g |
| formic acid | 50 mg |
| nonanol | 50 mg |
| surfactant (sulphonated castor oil) | 100 mg |
| heat to 65° C. | |

| Phase 2 | |
|---|---|
| abietoyloxyethyl acrylate | 2.5 g |
| hydrogen peroxide 30% | 0.3 ml |
| sodium thiosulphate 5% | 0.4 ml |
| heat to 70–75° C. | |

| Phase 3: | |
|---|---|
| add via dropping funnel in the course of 1 hour | |
| sodium thiosulphate 5% | 2.0 ml |
| abietoyloxyethyl acrylate | 23 g |
| temperature rises to 90–95° C. | |
| cool to 20° C. | |

A dispersion of poly(abietoyloxyethyl acrylate) with a solids content of 50% was obtained.

I claim:

1. An acrylate monomer complying with the formula:

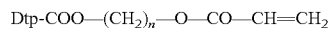

Dtp-COO—(CH$_2$)$_n$—O—CO—CH=CH$_2$ wherein

Dtp is a diterpene group derived from a resin acid and n is a number from 2–4.

2. The acrylate monomer according to claim 1, wherein n=2.

3. The acrylate monomer according to claim 1, wherein Dtp has an empirical formula C$_{19}$H$_{27}$, C$_{19}$H$_{29}$ or C$_{19}$H$_{31}$.

4. The acrylate monomer according to claim 3, wherein n=2.

5. The acrylate monomer according to claim 3, wherein Dtp is the decarboxylated radical of abietic acid or pimaric acid.

6. The acrylate monomer according to claim 5, wherein $n=2$.

7. A process for preparing the acrylate monomer according to claim 1, comprising reacting a resin acid with a hydroxyalkyl acrylate in the presence of an acid.

8. A construction adhesive comprising a diterpene acrylate monomer according to claim 1 or an oligomer or polymer or copolymer thereof.

9. The construction adhesive according to claim 8, further comprising 1–10 parts by weight of a conducting metal or conducting polymer per part by weight of diterpene acrylate monomer, oligomer, polymer or copolymer.

10. The construction adhesive according to claim 8, further comprising 0.05–1 part by weight of a monomer, oligomer or polymer of alkyl acrylate optionally substitute by hydroxyl, alkoxy or acyloxy and/or a silane acrylate per part by weight of diterpene acrylate monomer, oligomer, polymer or copolymer.

11. An emulsion polymer of a diterpene acrylate monomer according to claim 1.

* * * * *